(12) United States Patent
Towle

(10) Patent No.: US 9,023,468 B2
(45) Date of Patent: May 5, 2015

(54) METHOD FOR PREPARING POLY (ETHER KETONE KETONES)

(75) Inventor: Ian Towle, Gloucestershire (GB)

(73) Assignee: Ketonex Limited, Langley (GB)

( * ) Notice: Subject to any disclaimer, the term of this patent is extended or adjusted under 35 U.S.C. 154(b) by 424 days.

(21) Appl. No.: 13/383,171

(22) PCT Filed: Jul. 9, 2010

(86) PCT No.: PCT/GB2010/001318
§ 371 (c)(1),
(2), (4) Date: Jul. 3, 2012

(87) PCT Pub. No.: WO2011/004164
PCT Pub. Date: Jan. 13, 2011

(65) Prior Publication Data
US 2012/0263953 A1 Oct. 18, 2012

(30) Foreign Application Priority Data
Jul. 9, 2009 (GB) .................................. 0911905.8

(51) Int. Cl.
| | | |
|---|---|---|
| *A61L 27/18* | (2006.01) | |
| *C08L 71/12* | (2006.01) | |
| *C08G 61/12* | (2006.01) | |
| *D01F 6/66* | (2006.01) | |
| *C08L 65/00* | (2006.01) | |

(52) U.S. Cl.
CPC ............. *C08G 61/127* (2013.01); *A61L 27/18* (2013.01); *C08G 2261/3442* (2013.01); *C08G 2261/45* (2013.01); *C08L 65/00* (2013.01); *C08L 71/12* (2013.01); *D01F 6/665* (2013.01); *Y10T 428/2982* (2013.01)

(58) Field of Classification Search
USPC .................... 428/402; 525/242; 528/125, 180
IPC .......... A61L 27/18; C08G 61/127; D01F 6/665; C08L 71/12
See application file for complete search history.

(56) References Cited

U.S. PATENT DOCUMENTS

| | | | |
|---|---|---|---|
| 3,953,400 A | | 4/1976 | Dahl |
| 4,698,393 A | * | 10/1987 | Jansons et al. ................ 525/242 |
| 4,816,556 A | | 3/1989 | Gay et al. |
| 4,841,013 A | * | 6/1989 | Towle ........................... 528/125 |
| 4,912,181 A | | 3/1990 | Becker et al. |
| 4,990,589 A | | 2/1991 | Towle et al. |
| 5,145,938 A | | 9/1992 | Towle |
| 5,260,404 A | | 11/1993 | Whiteley et al. |
| 5,338,821 A | | 8/1994 | Towle |
| 5,734,005 A | | 3/1998 | Daniels et al. |

FOREIGN PATENT DOCUMENTS

| | | | |
|---|---|---|---|
| EP | 0174207 A2 | | 3/1986 |
| GB | 2287031 | * | 9/1995 |
| GB | 2287031 A | | 9/1995 |

OTHER PUBLICATIONS

International Search Report issued on Mar. 29, 2011 for International Application No. PCT/GB2010/001318.

* cited by examiner

*Primary Examiner* — Leszek Kiliman
(74) *Attorney, Agent, or Firm* — Knobbe, Martens, Olson & Bear, LLP

(57) ABSTRACT

A method of preparing a poly (ether ketone ketone) consisting essentially of the repeat unit:

—Ar—O—Ar—C(=O)—Ar—C(=O)— wherein each Ar is independently an aromatic moiety is provided. The method may comprise the step of polymerising a monomer system in a reaction medium comprising: (a) a Lewis acid; and (b) a controlling agent comprising an aromatic carboxylic acid, an aromatic sulphonic acid, or a derivative thereof.

17 Claims, 2 Drawing Sheets

METHOD FOR PREPARING POLY (ETHER KETONE KETONES)

CROSS-REFERENCE TO RELATED APPLICATIONS

This application is the U.S. National Phase of International Application No. PCT/GB2010/001318, filed Jul. 9, 2010, designating the U.S. and published as WO 2011/004164 on Jan. 13, 2011 which claims the benefit of British Patent Application No. 0911905.8 filed Jul. 9, 2009.

FIELD OF THE INVENTION

The present invention relates to a method of preparing poly ether ketones, in particular aromatic poly (ether ketone ketones) or "PEKKs".

BACKGROUND OF THE INVENTION

Poly ether ketones have a variety of useful properties, such as excellent electrical insulating and mechanical properties at high temperature, high strength, toughness and resistance to heat and chemicals. Such polymers may be amorphous or semi-crystalline. Both types usually exhibit high glass transition temperatures ($T_g$), while the semi-crystalline forms also exhibit high melting temperatures ($T_m$). Amongst these polymers, the poly (ether ketone ketone) family is of particular interest for use in preparing biomedical implants and implant materials due to their excellent mechanical properties, chemical inertness and resistance to stress cracking. The same materials are also useful in aerospace and many other wide-ranging industrial applications including the preparation of thermoplastic composites.

Common terminology involves naming such polymers by reference to the structure of the repeating unit (as is standard in polymer chemistry) with families being named according to the sequence of ether (symbolised by "E") and ketone (symbolised by "K") linkages in the repeat units. For example, polymers consisting essentially of the repeating unit: —R—O—R—C(=O)—R—C(=O)— would be referred to as "PEKK".

For in vivo use, PEKK materials must further meet the requirement of biocompatibility which, in turn, demands a high level of purity of the basic polymer. Ideally, it is required that these can be produced in essentially pure form on a large scale in the absence of substantial amounts of unreacted monomers, catalyst residues or other reaction components or contaminants. These impurities can also result in melt instability of the polymers during processing. This can be a serious problem during the preparation of composite materials as the instability can lead to property changes during manufacture that may impact performance in-use. For structurally critical applications, such as in aerospace, this is highly undesirable.

Aromatic polyetherketones are commonly prepared by either a nucleophilic or electrophilic polymerisation. For example, the polymer PEEK as supplied by Victrex Plc is understood to be synthesised by a high temperature nucleophilic process as depicted:

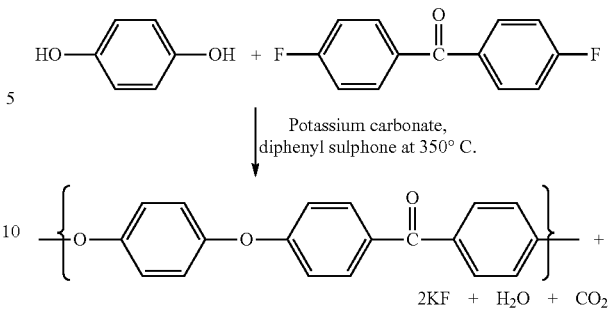

This type of reaction can be referred to as an ether-forming reaction as the result of the reaction is the formation of an ether linkage.

Alternatively, poly ether ketones such as PEKK may be formed using an electrophilic polymerisation as depicted. This is also commonly referred to as the Friedel-Crafts method.

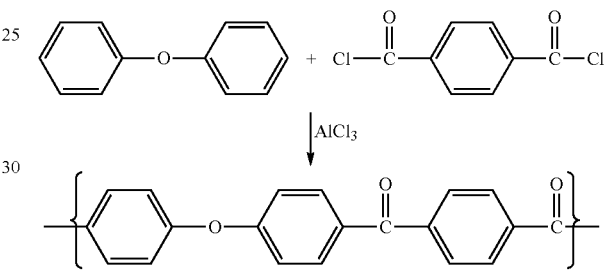

This type of reaction can be referred to as a ketone-forming reaction as the result of the reaction is the formation of a ketone linkage.

Unlike the nucleophilic reaction, the electrophilic or Friedel-Crafts reaction may be conducted at elevated temperature as disclosed in U.S. Pat. No. 4,816,556 or at ambient or sub-ambient temperature as taught in U.S. Pat. No. 4,841,013. Typical reaction media for these reactions include the reactants (i.e. the monomers), a catalyst (or promoter, e.g. $K_2CO_3$ or $AlCl_3$) and a suitable solvent.

The nucleophilic reaction is a solution reaction in that the growing polymer chain is maintained in a reactive state by the polymer remaining in solution (e.g. in diphenyl sulphone at elevated temperature). In contrast, the electrophilic reactions are not true solution reactions as the polymer is inclined to precipitate out as the chain length grows. Unlike a normal precipitation, the particles aggregate forming an intractable mass. The mobility of this mass is maintained in the process of U.S. Pat. No. 4,816,556 by the use of elevated temperatures and by the incorporation of a Lewis base in the process of U.S. Pat. No. 4,841,013 to form a deformable complexed gel structure in which there remains sufficient end-group mobility to enable polymerisation to continue.

Both the high temperature electrophilic and nucleophilic processes can produce products that exhibit poor melt stability resulting from side reactions. The very high temperatures used in the nucleophilic process can result in the scrambling of the ether and ketone linkages resulting in products in which the linkages are not as ordered as theory would predict or as desired. The high temperatures associated with these two processes can also promote side reactions and the formation of gels (probably cross-linked particles) that lead to melt instability in the final product. These gels may appear as discoloured inclusions. This makes the production of materials having a fine structure (e.g. fibres and thin films) difficult or, in some cases, impossible.

U.S. Pat. No. 4,912,181 discloses a low temperature electrophilic process which results in the formation of a complexed gel (with $AlCl_3$) and which requires the use of specialised equipment to facilitate the extraction of the final product from the reaction equipment. When practised correctly, this low temperature Friedel-Crafts process can produce a final product that is neither scrambled nor contaminated with side reaction products or imperfections (e.g. cross-linked gels) thus enabling the production of fine products such as fibres without the need for melt filtrations, or other gel removing protocols, prior to processing.

Typically, the organic moieties connecting the ether and ketone linkages in polyetherketones are aromatic units which are in themselves 1,4 or 1,3-disubstituted (1,2-disubstitution is known but is unusual). All 1,4 substituted polyetherketones exhibit high levels of crystallinity. In addition, the $T_m$ of the polymers increase as the ratio of ketones to ethers is increased. Thus the $T_m$ of 1,4-PEEK is around 345° C. and that of 1,4-PEKK is around 395° C. whilst both exhibit ultimate levels of crystallinity of between 35% and 40%. Although 1,4-PEKK can be readily synthesised by either of the aforementioned electrophilic processes, the high $T_m$, makes synthesis by the nucleophilic process difficult as the polymer is reluctant to remain in solution long enough for high molecular weight product to be formed. It is well known that the $T_m$, of all poly ether ketones can be manipulated by the incorporation of 1,3 units (and 1,2) in the structure such that suitable mixtures of 1,4 and 1,3 units can lead to the production of amorphous products. Whilst all 1,4-PEKK is difficult to melt process it can be solution processed from solvents such as concentrated sulphuric acid.

In order to facilitate the electrophilic synthesis of PEKK the reaction may be undertaken in strongly acidic solvent systems such as $HF/BF_3$ (see e.g. U.S. Pat. No. 3,956,240) or perfluoroalkyl-sulphonic acids (see e.g. U.S. Pat. No. 4,396,755). However, these solvent systems are highly corrosive and thus present handling problems. Alternative commercial methods for preparing 80:20 PEKK (80% 1,4: 20% 1,3) include the high temperature electrophilic process disclosed in U.S. Pat. No. 4,816,556. However, as mentioned above, this high temperature process can result in the production of an unstable product (high temperatures increase the likelihood of side reactions) containing imperfections (e.g. cross-linked gels), making it quite unsuitable for certain end uses, e.g. in biomedical implants, in producing articles having a fine structure and in critical aerospace composites.

U.S. Pat. No. 5,734,005 describes a modified Friedel-Crafts synthesis of polyetherketones using polymeric Lewis bases leading to the formation of high molecular weight products. It is believed that the use of these Lewis acid/Lewis base controlling agents alters the solubility parameter of the solvent such that the polymer complex remains in solution longer and yet still permits polymer chain mobility required for the production of high molecular weight products. The disadvantage of this process and that of the complexed gel products disclosed in U.S. Pat. No. 4,912,181 is the high cost of the specialised equipment required to handle the polymer gel complex. Additional disadvantages include the large volumes of water required to decomplex and work up the polymer, owing to its very low bulk density, and the difficulty in recovering most of the solvent or Lewis base.

The process of U.S. Pat. No. 4,841,013 employs protic controlling agents for the preparation of poly ether ketones, in particular PEKEKK. The authors note that it cannot be reliably predicted whether a particular controlling agent will act as a dispersant, this being dependent on other reactants and conditions. This is confirmed by the present inventor's own findings. In fact, the present inventor has found that for every 10 polymerisations carried out as described in U.S. Pat. No. 4,841,013 for PEKEKK production, on average only 1 results in the formation of a finely dispersed polymer product. The remaining polymerisations fail to provide the desired end product due to gel, or partial gel, formation. Efforts to address this in U.S. Pat. No. 4,841,013 include the incorporation of a second non-polar solvent such as cyclohexane. However, even this is found to be unreliable. Such a level of unpredictability is unacceptable, especially in a commercial process.

Whilst U.S. Pat. No. 4,841,013 discloses the production of PEKK using butanol as controlling agent, this may lead to alkylation of the polymer chain resulting in the formation of an unstable product. Moreover, the butanol is not recoverable.

U.S. Pat. No. 4,912,181 discloses a process by which the polymer complexed gels may be handled. Initial mixing and reaction is carried out in one reactor and prior to gel formation the reaction mixture is transferred to a tubular reactor where gelling occurs. On completion of polymerisation the gel is extruded from the tube into a hammer mill where decomplexation takes place in the presence of water leading to isolation of the polymer. Although high quality products can be manufactured in this way, the process requires special equipment and thus suitably adapted large scale plants for commercial production, making this method costly.

To date, despite its advantageous properties, the issues outlined above have made the large scale production of highly pure and melt-stable PEKKs problematic.

SUMMARY OF INVENTION

There thus exists a need for improved methods for preparing poly (ether ketone ketones) (PEKKs), in particular methods which do not require special equipment and handling techniques, yet which can produce a product which on work-up is largely free from reaction impurities. Preferably, such methods would include one where the polymer is readily dispersed in the reaction medium, thus avoiding the need for specialised reactors such as tubular ones, where the majority of non-polymerising components can be recovered for future use and where the amount of water used in the material isolation is minimised whilst still producing high quality highly stable products.

BRIEF DESCRIPTION OF THE DRAW1NGS

DETAILED DESCRIPTION OF THE EMBODIMENTS

Figure 1:
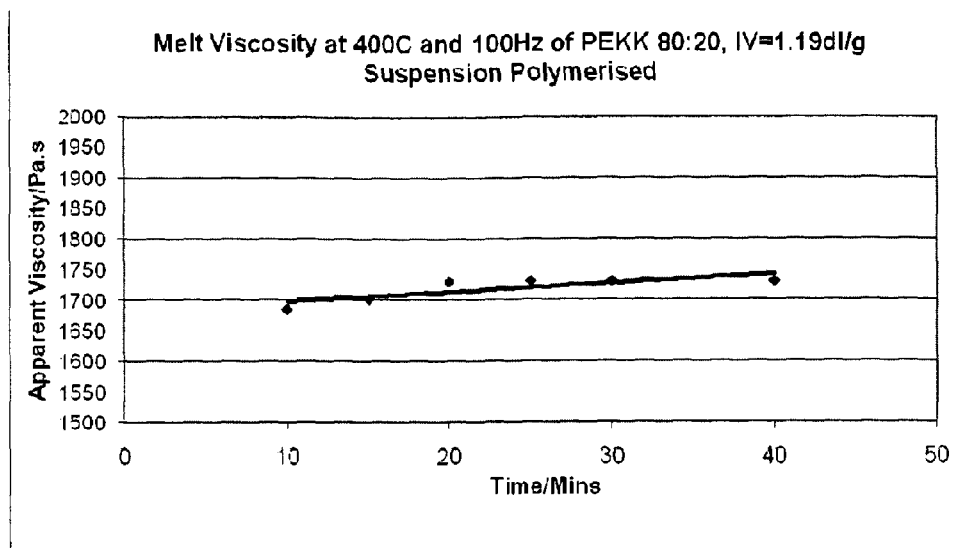
FIG. 1 illustrates data showing that the melt viscosity of the polymers produced according to the methods outlined herein does not increase significantly over 40 minutes at 400° C and 100 Hz.

The present inventor has found that the propensity of particular controlling agents to act as dispersants, rather than to form complexed gel structures, is influenced by the sequence of ether and ketone groups found in the repeating units of the final polymer material. This means that suitable controlling agents for particular polymer syntheses cannot be reliably predicted.

Surprisingly, it has now been found that the use of certain controlling agents, such as benzoic acid and its derivatives, in PEKK production gives the desired suspension and facilitates the removal of the solvent and the controlling agent in work-up of the final product. This allows a stable reaction product to be achieved in a controlled and reliable manner, thus enabling production on a commercial scale. As will be demonstrated herein, PEKK material manufactured according to this method has been found to exhibit almost zero change in melt viscosity at 400° C. and at a shear rate of 100 Hz over 40 minutes.

Thus, viewed from a first aspect, the present invention provides a method of preparing a poly (ether ketone ketone) consisting essentially of the repeat unit:

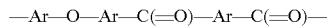

wherein each Ar is independently an aromatic moiety,
said method comprising the step of polymerising a monomer system in a reaction medium comprising:
(a) a Lewis acid; and
(b) a controlling agent comprising an aromatic carboxylic acid, an aromatic sulphonic acid, or a derivative thereof.

Each aromatic moiety in the polymer repeating unit (Ar) is independently selected from substituted and unsubstituted phenylene and substituted and unsubstituted polynuclear aromatic moieties. The term "polynuclear" is considered to encompass fused aromatic rings such as naphthalene and non-fused rings such as biphenyl, etc. Particularly preferably, Ar is phenylene.

The phenylene and polynuclear aromatic moieties (i.e. "Ar") may contain substituents on the aromatic rings. Such substituents would be readily understood by the skilled person and should not inhibit or otherwise interfere with the polymerisation reaction to any significant extent. Typical substituents may include, for example, phenyl, halogen (e.g. F, Cl, Br, I), ester, nitro, cyano, alkyl (e.g. $C_{1-6}$ alkyl) and the like.

The method of the invention employs controlling agents which are aromatic carboxylic acids, aromatic sulphonic acids or derivatives thereof. Such acids may comprise 1, 2 or 3 carboxylic or sulphonic acid groups on an aromatic ring (i.e. these may be mono-, di- or tri-acids). Derivatives of such acids include metals salts and esters.

Preferred controlling agents for use in the method of the invention include the following:
(i) Ar'(COOX)$_y$;
(ii) Ar'(SO$_3$X)$_y$;
(iii) (Ar'COO$^-$)$_z$M$^{z+}$; or
(iv) (Ar'SO$_3^-$)$_z$M$^{z+}$
wherein Ar' is an aromatic group compatible with the remaining components of the reaction medium;
each X independently is a hydrogen atom or an organic group (R);
each y independently is 1, 2 or 3;
each M independently is a metal ion and
each z independently is an integer equal to the charge on the metal ion (M$^{z+}$).

The aromatic group of the controlling agent (i.e. Ar') may be selected from substituted and unsubstituted phenyl and substituted and unsubstituted polynuclear aromatic moieties. Preferably the aromatic group of the controlling agent is an optionally substituted phenyl group. Preferred substituents may include halogen (e.g. F, Cl, Br, I), nitro, cyano, alkyl (e.g. $C_{1-6}$ alkyl) and the like. Alkyl substituents are preferred, e.g. methyl, ethyl, etc. Where substituents are present, these are preferably electron-withdrawing groups which deactivate the ring to electrophilic attack.

When X=R, the organic group R is preferably a straight-chained or branched $C_{1-6}$ alkyl group, i.e. the controlling agent is an alkyl ester of an aromatic carboxylic acid or aromatic sulphonic acid. More preferably, R is $C_{1-4}$ alkyl. e.g. methyl.

Especially preferred controlling agents for use in the invention include benzoic acid, methyl benzoic acid, sodium benzoate, magnesium benzoate, aluminium benzoate, methyl benzoate and benzene sulphonic acid. Particularly preferably, the controlling agent is benzoic acid.

Mixtures of two or more controlling agents may also be used, if desired.

The amount of controlling agent present is preferably from 0.1 to 5 equivalents per equivalent of acid halide groups present in the monomer system. Amounts greater than 5 equivalents could be employed, if desired, e.g. up to 10 equivalents, e.g. 7 equivalents. However, no additional controlling or dispersing effect is usually achieved by adding larger amounts and it generally means that more Lewis acid is also required. Thus, it is preferred to use no more than 5 equivalents, more preferably between 0.5 and 4 equivalents and especially between 0.5 and 2 equivalents per equivalent of acid halide groups. The actual amount of controlling agent added depends upon, inter alia, the particular controlling agent used, the nature of the monomers present and the type and amount of Lewis acid employed. The ranges given particularly apply to the controlling agents containing one carboxylic acid or sulphonic acid functionality, e.g., those listed as (i) to (iv) above where y or z is equal to 1. For those controlling agents containing more than one acid group per molecule, e.g. where y or z is not 1, the equivalents of controlling agent to acid halide groups in the monomer systems may be adjusted accordingly.

As previously discussed, many of the prior art polymerisation processes which employ controlling agents are unreliable to the extent that it cannot be predicted whether a complexed gel or dispersion will result. Mixed solvent systems have been used in order to promote dispersion over gel formation. Whilst such systems may be used in the methods herein described, this is not essential to achieve the desired effects. The present process therefore allows the use of a single solvent (e.g. dichloromethane) which makes solvent removal easier; the dispersion of droplets is easier to control, e.g. benzoic acid can give dispersions of the polymer PEKK in pure dichloromethane without the need for further diluents such as cyclohexane. The fact that solvent mixtures are not required makes solvent removal easier (e.g. dichloromethane can be distilled off at 41° C. with extremely high recovery rates).

Moreover, controlling agents such as benzoic acid can also be readily recovered for future use when carrying out the method of the invention. The recovery of the controlling agent benzoic acid is facilitated by the fact that the acid has very low solubility in cold water but high solubility in hot water. Thus after heating the polymer slurry in water after decomplexation, the polymer can be recovered by filtration and on allowing the filtrate to cool the benzoic acid crystallises out facilitating its recovery for future use. An alternative method to recover the benzoic acid would be to add sufficient sodium hydroxide to form sodium benzoate which is water soluble (1 g in 2 mL of water), filter and isolate the polymer and then add an acid such as hydrochloric acid to the filtrate to reform benzoic acid which would precipitate from the filtrate.

A further advantage of the invention is the reduction in the amount of water necessary to remove the catalyst residues and controlling agents when compared to that necessary using the gel and tube process. In the complexed gel and tube process the polymer after decomplexation has a very low bulk density, sometimes as low as 0.08 g/mL, thus requiring the use of large work-up vessels and large quantities of water to afford a mobile slurry. Using the dispersion method of the invention the bulk density of the isolated polymer is much higher thus permitting the use of much lower volume work-up vessels and significantly reducing the amount of water required to purify the isolated polymer.

The ability to recover the solvent and the controlling agent and the reduction in the amount of water required in the process provides a more sustainable and cost-effective process than the prior art methods which require solvent mixtures, controlling agents which are difficult to remove and large quantities of water.

Without wishing to be bound by theory, it is thought that the controlling agents which are used in the method of the invention either do not participate in the reaction (unlike the butanol of the prior art which may cause alkylation), or, if they do participate in the reaction, they give the desired product (this can be ensured by selecting a controlling agent where Ar'=Ar). For example, a controlling agent such as trifluoroacetic acid can potentially take part in the polymerisation reaction as a chain terminator. This would result in a PEKK product with trifluoroacetyl end groups which could potentially be undesirable. In the event that controlling agents such as benzene carboxylic acids or benzene sulphonic acids take part in the polymerisation reaction then the PEKK product would have either benzoyl or benzene sulphonyl end groups. Both of these end groups are highly stable and, as shown in the examples, benzoyl chloride may actually be added to control both molecular weight growth and to provide stable end groups. Thus, should benzoic acid take part in the polymerisation this would have no detrimental effect on the quality of the polymer produced.

Furthermore, because the present invention avoids the production of a complexed gel, the special reactors and handling protocols required for the methods involving gel production are not required, thus reducing cost.

Another advantageous aspect of the present invention is the work-up of the polymer following completion of the reaction. In general it is necessary to remove all components (e.g. the catalyst, solvent and any other components) before the resulting polymer can be used. In the prior art processes which involve complexed gel production this is effected by homogenising the resulting complexed polymer with large amounts of water and ice. This produces a coarse fibrous powder of very low bulk density and thus very large vessels (and large amounts of water) are required to clean up the material. In contrast, the product from the suspension process of the present invention is much denser thus enabling the use of much smaller vessels and less water.

The process can be carried out in a manner similar to standard suspension polymerisation reactions. The reactions are generally carried out in an inert atmosphere, e.g. reaction vessels may be purged with nitrogen or argon. Typically, the catalyst is added to a solution or slurry (preferably cooled to well below room temperature, e.g. −20° C.) of one or more monomers in a suitable solvent (e.g. dichloromethane). Further monomer or monomer mixtures, if required, may then be added in a solution of the same solvent or as solids. The controlling agent may be added earlier or later in the sequence of additions, provided the temperature of the slurry is kept below −10° C. during the addition, preferably below −20° C. Additional reaction components, e.g. capping agents, additional diluent etc., are typically also added at this stage.

The resulting reaction mass is then typically allowed to warm towards room temperature while being stirred vigorously in a suitably baffled reactor. During the polymerisation, any by-products (e.g. hydrogen chloride) can be trapped and disposed of. After stirring at room temperature for a suitable length of time (in general 4 to 8 hours, preferably 6 hours) work-up/decomplexation can begin by combining the entire reaction mass with decomplexing base (e.g. iced water). Care must be taken to avoid the temperature of the decomplexing mixture rising above room temperature. Prior to decomplexation the reaction mass is typically an orange slurry and after complete decomplexation the mass is usually a snow white slurry. The mass is then typically stirred at or below room temperature to yield the final polymer product.

Solvent removal from this product may be carried out by any conventional method, although typically this will be by distillation. Further purification can be achieved by known methods, e.g. hot filtration of the suspension to yield the polymer product, typically as a snow white residue. Cooling of the combined filtrates (e.g. to 5° C.) results in recovery of the controlling agent by crystallisation. Using this method, up to 95% of the solvent, usually dichloromethane, can be recovered along with up to 90% of the controlling agent (e.g. when the controlling agent is benzoic acid or a benzoic acid derivative).

The monomer system used in the methods herein described comprises monomers suitable for polymerisation or co-polymerisation in order to produce a polymer consisting essentially of the repeat unit —Ar—O—Ar—C(=O)—Ar—C(=O)—. Such monomer systems and combinations would be readily apparent to the person skilled in the art.

Preferred monomers may include but are not restricted to:

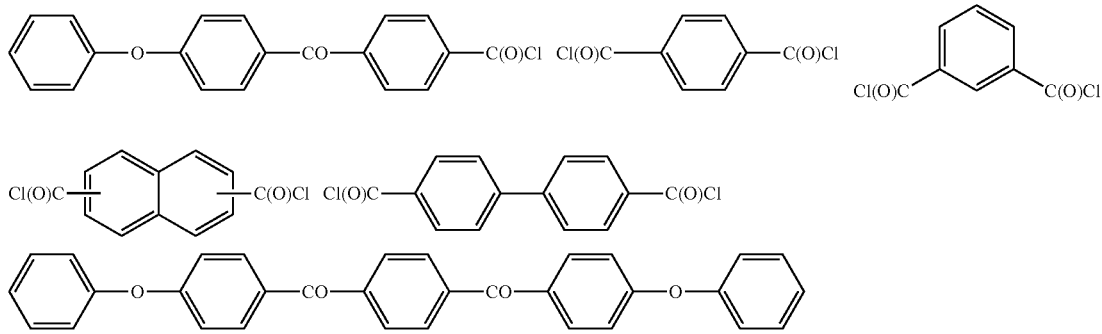

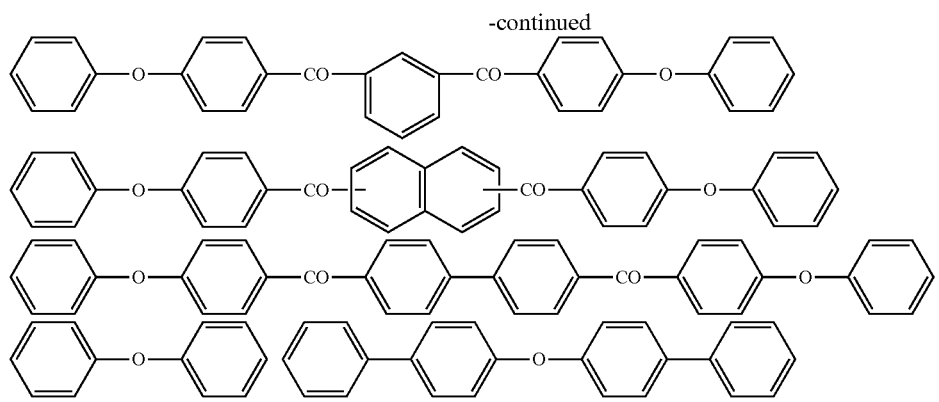

Preferred capping agents include:

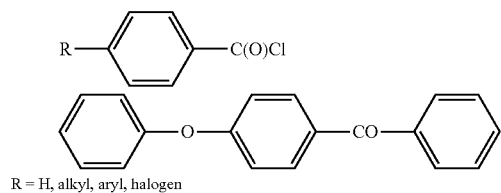

R = H, alkyl, aryl, halogen

Whilst the above-listed chlorides are preferred, other acid halides, particularly the fluorides and the bromides, may also be used. Generally, the chlorides are preferred due to their availability and reactivity. Other groups that are potentially displaceable under Friedel-Crafts conditions may also be used. These might include groups such as —OR, where R is methyl, ethyl, isopropyl or other lower alkyl.

The combinations of monomers suitable for producing the polymer materials herein described would be readily apparent to a person skilled in the art, as would the relative proportions of the monomers. For example, monomers with repeating units "EKK" can be polymerised alone, i.e. without a co-monomer, to produce PEKK.

The proportion of 1,4-linked aromatic (e.g. phenyl) rings in PEKK greatly influences the characteristics of the resulting polymer (e.g. its processability, etc.). Depending on the intended use for the polymer produced, the characteristics can be modified by changing the proportion of 1,4-linked aromatic rings in the polymer. This may be achieved by the use of monomers comprising 1,3-substituted aromatic rings. For example, isophthaloyl halides such as isophthaloyl chloride can be used as monomers and the amounts chosen in relation to the other monomers in order to produce a polymer with the desired characteristics. Preferably the monomers are chosen such that the proportion of 1,3-linked aromatic rings in the resulting polymer is 0 to 100%, more especially 5 to 50%, particularly 20 to 40%, e.g. about 30%. All percentages and ratios are by weight, unless otherwise specified.

Particularly preferably the monomer system comprises b is 1,4(4-phenoxybenzoyl)benzene and terephthaloyl halide and isophthaloyl halides (e.g. a 60:40 mixture of tere- and iso-phthaloyl chloride) in a 1:1 ratio by weight. This would produce an 80:20 polymer, i.e. the iso-linked units would be present in 20% by weight in the final polymer material.

The temperature at which the reaction is conducted can be from about −50° C. to about +150° C. It is preferred to start the reaction at lower temperatures, for example at about −50° C. to about −10° C., particularly if the monomer system contains highly reactive monomers. After polymerisation has commenced, the temperature can be raised if desired, for example, to increase the rate of reaction. It is generally preferred to carry out the reaction at temperatures in the range of between about −30° C. and +25° C.

In the methods herein described, a Lewis acid is used as catalyst. The term "Lewis acid" is used to refer to a substance which can accept a shared electron pair from another molecule. Suitable catalysts for use in the method of the invention include aluminium trichloride, aluminium tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Preferably the catalyst is substantially anhydrous aluminium trichloride.

The amount of Lewis acid catalyst used will vary depending on the particular monomers and the reaction medium selected. Typically, the amount of Lewis acid required is calculated on the basis of one Lewis acid for each ketone unit, plus an amount equimolar to that of Lewis base, or controlling agent, plus up to 20% excess. Larger excesses can be used but offer no significant advantage.

Preferred solvents for the polymerisation reaction are halogenated hydrocarbons (e.g. tetrachloroethylene, 1,2,4-trichlorobenzene, o-difluorobenzene, 2-dichloroethane dichlorobenzene, 1,1,2,2,-tetrachloroethane, particularly ortho-dichlorobenzene, dichloromethane etc.). Additionally, or alternatively, non-chlorinated diluents may be used such as cyclohexane, carbon disulphide, nitromethane, nitrobenzene, HF. Dichloromethane is particularly preferred for use in the present invention.

If necessary, capping agents may be added to the polymerisation reaction medium to cap the polymer on at least one end of the polymer chain. This terminates continued growth of that chain and controls the resulting molecular weight of the polymer. Use of the capping agents may therefore be used to produce polymers within a selected narrow molecular weight range. Both nucleophilic and electrophilic capping agents may be used to cap the polymer at each end of the chain.

Preferred nucleophilic capping agents are 4-chlorobiphenyl, 4-phenoxybenzophenone, 4-(4-phenoxyphenoxy)benzophenone, biphenyl 4-benzenesulphonylphenyl phenyl ether, and the like. Typical electrophilic capping agents include benzoyl chloride, benzenesulfonyl chloride and the like.

A non-protic diluent can also be employed, if desired. Advantageously, the diluent should be inert towards Friedel-Crafts reactions. Other diluents include, for example, dichloromethane, carbon disulphide, o-dichlorobenzene (i.e. ortho- or 1,2-dichlorobenzene), 1,2,4-trichlorobenzene, o-difluorobenzene, 1,2-dichloroethane, cyclohexane, 1,1,2,2,-tetrachloroethane and mixtures thereof. Whilst these additional diluents may be used they confer no significant advantage to the process and may result in difficulty in separating the diluents used for further use. A process which is substantially free from co-solvent is therefore a preferred aspect of the present invention.

The amount of any diluent used is most preferably in the range of 50 mL to 200 mL of diluent to 10 g of polymer. Both higher and lower concentrations may be used if required.

When Friedel-Crafts polymerisation is complete, the polymer contains Lewis acid catalyst complexed to any carbonyl groups. The catalyst residue must be removed, i.e. the Lewis acid must be decomplexed from the polymer and removed. Decomplexation can be accomplished by treating the polymerization reaction mixture with a decomplexing base after completion of polymerization. The decomplexing base must be at least as basic towards the Lewis acid as the basic groups on the polymer chain. Such decomplexation should be effected before the isolation of the polymer from the reaction mixture.

The amount of decomplexing base used should be in excess of the total amount of bound (complexed) and unbound Lewis acid present in the reaction mixture and is preferably at least twice the total amount of Lewis acid. Typical decomplexing bases which can be used include water, dilute aqueous hydrochloric acid, methanol, ethanol, acetone, N,N-dimethylformamide, N,N-dimethylacetamide, pyridine, dimethyl ether, diethyl ether, tetrahydrofuran, trimethylamine, trimethylamine hydrochloride, dimethyl sulphide, tetramethylene sulphone, benzophenone, tetramethylammonium chloride, isopropanol, and the like. Iced water or cooled dilute hydrochloric acid are preferred for use in the present invention.

The polymers produced according to the methods outlined herein are of high quality exhibiting good melt stability. For example, as shown in FIG. 1, it has been found that the melt viscosity does not increase significantly over 40 minutes at 400° C. and 100 Hz.

As mentioned above, one of the advantages of the present invention is that poly(ether ketone ketones) of high molecular weight can be obtained, i.e. the controlling agents of the present invention avoid many of the problems found in the prior art. By "high molecular weight" is meant polymer having an inherent viscosity greater than about 0.4 dL/g. Preferably the polymers prepared by the method of the invention have inherent viscosities in the range of 0.6 to about 2.5 dL/g, more preferably in the range 1.0 to 1.5 dL/g.

Figure 2:
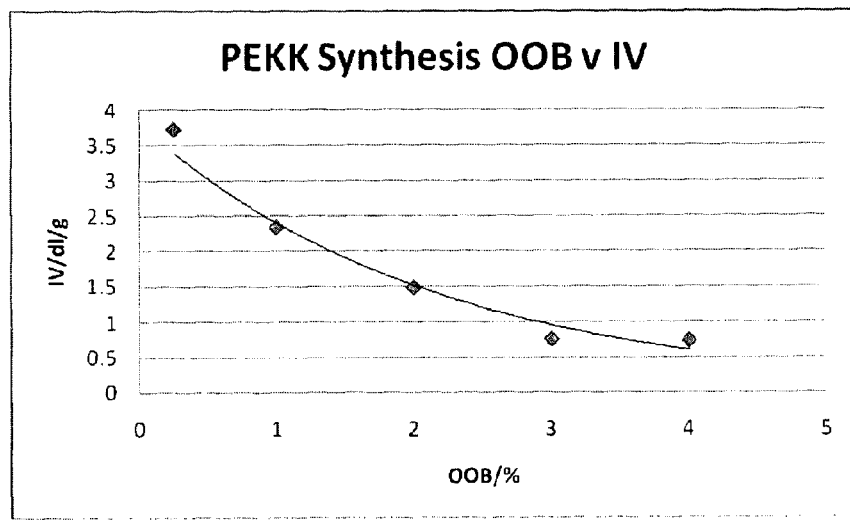
FIG. 2 illustrates data showing that PEKK polymers having IV in excess of 3.5 dL/g have been successfully synthesized according to the methods outlined herein.

The method of the present invention makes it possible to produce polymers with high inherent viscosities (IV) when using "in balance" reactions, i.e. where the correct stoichiometry is used. As illustrated in FIG. 2, PEKK polymers having IV in excess of 3.5 dL/g have been successfully synthesised by the invention. Whilst these polymers are not melt processable they may be processed by other methods, for example solution methods. Should polymers of lower IV values be required, the IV value of the product can be suitably adjusted by conducting the reaction "out of balance" (OOB). OOB reactions are commonly used in the art because in balance reactions can produce polymers with molecular weight values which are much higher than desired. The percentage by which the reaction is "out of balance" is the weight percent difference in the reactants from perfect (1:1) stoichiometry. FIG. 2 shows the IV values for 80:20 PEKK, synthesised as in Example 2, as a function of the degree of out of balance (OOB %). The fact that the plot shows a relationship between IV and OOB which obeys theory is evidence that the reactions of the present invention are extremely controllable. The plot may be used to calculate the exact proportion of reactants (i.e. the degree to which the stoichiometry is out of balance) required in order to give any desired IV value. A further aspect of the process of the present invention is thus that it allows the IV value of the resulting polymer to be determined by selecting the appropriate proportions of monomers.

The polymers produced by way of the methods herein described are considered to form a further aspect of the invention. For example, as the process of the invention allows the removal of solvent and controlling agent, the present invention also provides PEKK polymers which are essentially free of these components. Thus, in a further aspect, the present invention provides a poly (ether ketone ketone) consisting essentially of the repeat unit: —Ar—O—Ar—C(=O)—Ar—C(=O)— obtainable by any process as herein described.

Figure 4:
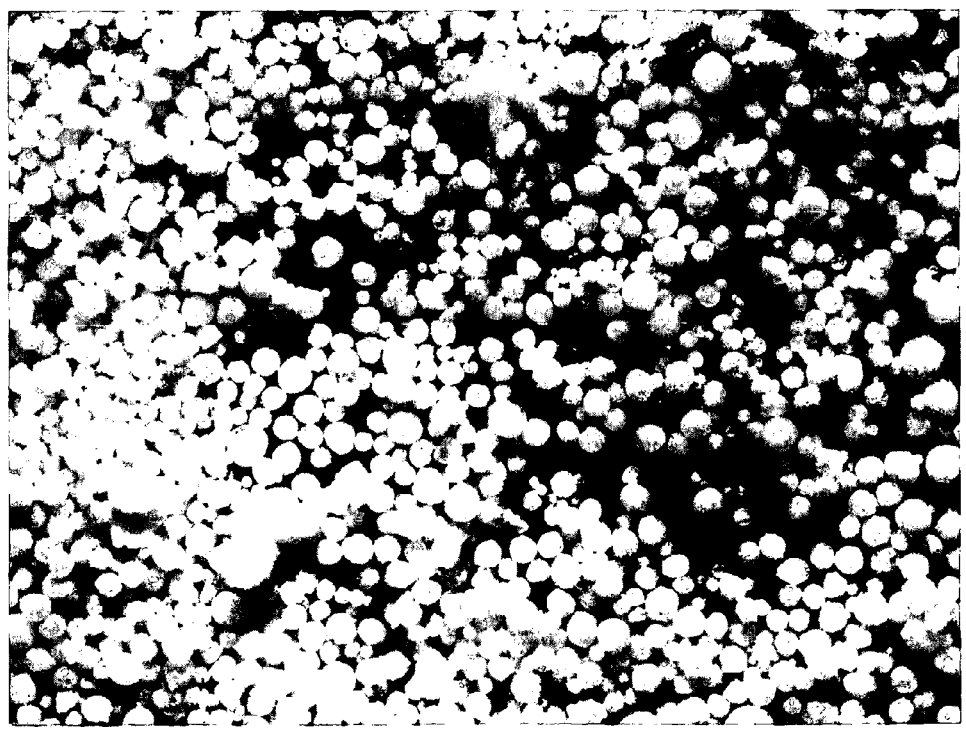
FIG. 4 shows a photograph taken using a Nikon Eclipse E400 optical microscope of a sample of the dried polymer powder.

A further advantage of the present invention is that the process can yield polymer particles, e.g. spheres of PEKK. The provision of spherical particles directly from the polymer production process is particularly advantageous as it means that costly further processing steps such as grinding and sieving are not necessary. Instead, the process gives spherical particles directly. Moreover, as shown in FIG. 4, the spherical particles produced according to the invention are more uniform in shape rather than the rough particulates that would be produced by grinding.

Particles of PEKK have, until now, been unobtainable, and thus form a further aspect of the present invention. Therefore, viewed from a further aspect, the invention provides particles, e.g. spherical or substantially spherical particles of PEKK.

By "particle size" is meant particle diameter. The particles according to the invention advantageously have particle sizes (e.g. as measured with a Coulter particle size analyser) of 0.1 to 3000 µm, preferably 1 to 500 µm, especially preferably 10 to 200 µm, e.g. 50 to 100 µm.

Typically, at least 25% (by volume) of the particles are less than 100 µm in diameter, preferably at least 50%, e.g. at least 75%. Alternatively, or additionally, at least 20% of the particles are less than 70 µm, preferably at least 40%, e.g. at least 60%.

The particles preferably have a coefficient of variation (CV) of less than 20%, e.g. less than 10%, more preferably less than 5%, still more preferably less than 2%. CV is determined in percentage as, CV=100×standard deviation mean where mean is the mean particle diameter and standard deviation is the standard deviation in particle size. CV is preferably calculated on the main mode, i.e. by fitting a monomodal distribution curve to the detected particle size distribution. Thus some particles below or above mode size may be discounted in the calculation which may for example be based on about 90% of total particle number (of detectable particles that is). Such a determination of CV is performable on a Coulter LS 130 particle size analyzer.

The size of the polymer particles may be controlled by varying the amount of dispersant added, amount of polymer per unit volume of solvent, the stirrer speed, the stirrer paddle design, temperature ramp rate, the reactor design and/or the addition of baffles to create turbulence. Other techniques well known in dispersion polymer chemistry may be employed. However, the present inventor has surprisingly found that, not only can the present invention provide spherical particles of PEKK for the first time, but the method allows the particle size (e.g. distribution and/or mean) to be controlled by varying the amount of controlling agent used.

It has been found that increasing the amount of controlling agent relative to the amount of monomers results in the average particle size decreasing. Typical ranges of ratio of moles of controlling agent to moles of acid halide groups present in the monomer system are from 0.1 to 10, preferably 0.5 to 7, especially 0.7 to 5, particularly preferably 1.5 to 2. The actual amount of controlling agent added depends upon, inter alia, the particular controlling agent used, the nature of the monomers present and the type and amount of Lewis acid employed. As noted above, the ranges given particularly apply to the controlling agents containing one carboxylic acid or sulphonic acid functionality, e.g., those listed as (i) to (iv) above where y or z is equal to 1. For those controlling agents containing more than one acid group per molecule, e.g. where y or z is not 1, the equivalents of controlling agent to acid halide groups in the monomer systems may be adjusted accordingly.

The higher relative amounts of controlling agent can produce particles of a smaller mode particle size than the lower amounts of controlling agent. It has been found that controlling the particle size is particularly suited to PEKKs in which the 1,4-linked units are present in 50% or more by weight.

As well as decreasing the size of the particles produced, increasing the relative amount of controlling agent used can result in extremely small particles being formed. For example, particles of less than one micron, i.e. as small as 0.275 μm were present in Sample 25 (see Example 7). If very small particles are desired, the amount of controlling agent (and/or other factors known to influence particle size in polymerisation reactions) can be chosen to optimise the amount of smaller particles and the smallest particles removed from the product mixture, e.g. by using conventional techniques such as sieving, air classification (e.g. air elutration), photoanalysis, optical counting methods, electroresistance counting methods, sedimentation techniques, laser diffraction methods, acoustic spectroscopy, ultrasound attenuation spectroscopy etc.

By varying the amount of controlling agent and separating the particles based on their size, the present invention allows PEKK of graded particle sizes to be produced. This lends the polymer to a variety of different applications as the size range of the particles can be controlled to suit the end use. For example, very small (e.g. sub-micron particles) could be used for powder impregnation of composites.

Thus the present invention provides a method for producing a poly (ether ketone ketone) consisting essentially of the repeat unit: —Ar—O—Ar—C(=O)—Ar—C(=O)— wherein each Ar is independently an aromatic moiety, having a selected particle size distribution, said method comprising the following steps:
(i) polymerising a monomer system in a reaction medium comprising:
  (a) a Lewis acid; and
  (b) a controlling agent comprising an aromatic carboxylic acid, an aromatic
  sulphonic acid, or a derivative thereof
and
(ii) adjusting the ratio of controlling agent to monomers in the monomer system whereby to control particle size distribution.

Preferably, the particle size is selected by adjusting the ratio of moles of controlling agent to moles of acid halide groups present in the monomer system. Typical ratios of moles of controlling agent to moles of acid halide groups present in the monomer system are from 0.1 to 10, preferably 0.5 to 7, especially 0.7 to 5, particularly preferably 1.5 to 2.

The above-mentioned polymers and spherical particles of polymer form a further aspect of the present invention, as do their uses and articles/composites comprising them. The present invention thus provides particles, e.g. substantially spherical particles, of a poly (ether ketone ketone) consisting essentially of the repeat unit: —Ar—O—Ar—C(=O)—Ar—C(=O)— wherein each Ar is independently an aromatic moiety.

A further aspect of the invention is a composition comprising spherical particles of PEKK. The compositions may comprise the particles in a suitable matrix, for example another polymer, such as a thermoplastic or thermoset. The particles can also be utilised as the powders in powder impregnated fibre composites. Other applications would include polymer powders used in flame spraying or selective laser sintering (SLS processing) and the like.

The polymer particles may be solid, hollow or porous. In the case where porous or hollow particles are formed, these may be used to encapsulate or support materials, e.g. active agents in order to impart extra functionality to the polymer.

The PEKK particles of, and produced according to, the invention preferably have the particle size characteristics referred to above.

The polymers of the invention may be blended with other polymers in order to produce polymer blends suited to a variety of purposes. Moreover, articles comprising the polymers of the invention form a further aspect of the invention.

In comparison with the processes of the prior art, the present invention produces polymers which are relatively free from impurities such as solvents, controlling agents or by-products of the polymerisation process. The polymers of the invention are thus particularly suitable for the production of biomedical implants and components thereof, e.g. spinal implants, hip implants and the like. Biomedical devices, e.g. implants or implant components, comprising a PEKK prepared by the methods as herein described thus form a further aspect of the present invention.

The excellent mechanical properties of PEKKs and the lack of impurities of the polymers makes them also suitable for use in the production of articles for which mechanical strength is paramount such as composites, e.g. aerospace composites and other articles for aerospace applications. For example, the polymers can be used as a resin matrix for carbon fibre or glass fibre composites and laminates, etc.

The fact that they lack the melt-instability found in the products of the prior art, makes the polymers of the invention particularly suitable for melt spin processing and thus they can form fine fibres (e.g. 10 to 50 microns in diameter). Furthermore, the polymers of the present invention are also capable of forming thin films (e.g. films of 100 microns or less in thickness) and these form a further aspect of the present invention. These properties lend themselves to the use of the polymers in the production of articles requiring a fine structure. For example due to the excellent temperature characteristics of PEKK, such fibres can be used in the production of high temperature filters, for example fly ash filters in power stations.

The invention will be further illustrated by way of the following non-limiting Examples:

EXAMPLE 1

Synthesis of 80:20 PEKK in Balance

To a 700 ml reaction flask equipped with a mechanical stirrer, having been purged with dry nitrogen, was added 41.5608 g (0.08833 mol) of pure 1,4-bis(4-phenoxybenzoyl) benzene along with 300 ml of dichloromethane. Having cooled the slurry to −20° C., 100 g (0.75 mol) of anhydrous aluminium trichloride was slowly added so as not to raise the temperature of the slurry above −10° C. and to minimise any splashing up the walls of the reactor. After cooling back to −20° C., 17.9328 g (0.08833 mol) of a mixture of isophthaloyl chloride (7.1463 g) and terephthaloyl chloride (10.7865 g) was added to the slurry along with a further 100 ml of dichloromethane. Also at −20° C., 31.75 g (0.26 mol) of benzoic acid was added.

Whilst stirring at 100 rpm the reaction mass was allowed to warm towards room temperature without additional heating. During this period, the colour of the reaction mass changed from yellow to pale orange. As the mass showed signs of phase separating, the speed of the stirrer was raised to 350 rpm and this speed was maintained for the duration of the synthesis. During the polymerisation, hydrogen chloride was evolved which was trapped and disposed of safely.

After stirring at room temperature for 6 hours the reaction mass was poured into 5 litres of iced water (care must be taken to avoid the temperature of the decomplexing mixture rising above room temperature). The aqueous mass was then stirred at room temperature for 4 hours or until all of the orange colouration had disappeared leaving a snow white mass.

Having transferred the white mass to a suitable vessel, the vessel was heated and the dichloromethane distilled off. The yield of the recovered dichloromethane was 94% by weight. Having removed all of the dichloromethane, the mass was brought to reflux and refluxed for 1 hour whereupon the suspension was filtered whilst hot. While the filtrate was left to cool the white polymer solid was added to a further 3 litres of deionised water and brought to reflux. This was repeated a further two times and in each case the filtrate was added to the initial filtrate and allowed to cool. The polymer powder was then dried overnight at 150° C. under a partial vacuum. On cooling, benzoic acid crystallised from the combined filtrates. The yield of benzoic acid was enhanced by chilling the filtrates to 5° C. The yield of the recovered benzoic acid was 75% by weight.

The Inherent Viscosity (IV) of the polymer was determined by dissolving approximately 25 mg of the polymer in 25 ml of concentrated sulphuric acid at 25° C. The IV of this sample was 2.34 dL/g. The structure of the polymer was confirmed by $^{13}$C NMR and showed the presence of the following repeat unit:

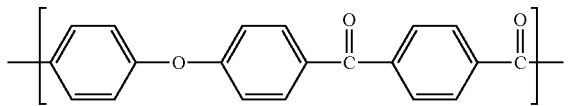

EXAMPLE 2

Synthesis of 80:20 PEKK 2.24% Out of Balance

The technique used was identical to that described in Example 1, but with the additional use of benzoyl chloride as a capping agent (which was added to the polymerisation mixture immediately after the benzoic acid). The reagents used were:

1,4-bis(4-phenoxybenzoyl)benzene: 50.6331 g (0.1076 mol)
Isophthaloyl and terephthaloyl chlorides: 21.3577 g (0.1052 mol)
  Isophthaloyl chloride: 8.7000 g
  Terephthaloyl chloride: 12.6577 g
Benzoic acid: 39.42 g (0.3228 mol)
Aluminium trichloride: 118.98 g (0.8923 mol)
Benzoyl chloride: 0.6747 g (4.8×10$^{−3}$ mol)
Dichloromethane: 450 ml The IV of the resultant polymer was 1.19 dL/g and the polymer had a viscosity of 1750 Pa·s at 400° C. and 100 Hz. The polymer was highly stable over 30 minutes at 400° C. The Tg was 165° C. and the Tm was 367° C. The yield of recovered dichloromethane and benzoic acid was similar to that in Example 1

EXAMPLE 3

Synthesis of 80:20 PEKK in Balance

The technique used was identical to that described in Example 1, except the benzoic acid controlling agent was replaced by benzene sulphonic acid. The reagents used were:
1,4-bis(4-phenoxybenzoyl)benzene: 40.2923 g (0.08563 mol)
Isophthaloyl and terephthaloyl chlorides: 17.3853 g (0.08563 mol)
  Isophthaloyl chloride: 7.3285 g
  Terephthaloyl chloride: 10.0568 g
Benzene sulphonic acid: 41.08 g (0.26 mol)
Aluminium trichloride: 83.8 g (0.63 mol)
Dichloromethane: 400 ml The IV of the resultant polymer was 2.40 dL/g. The yield of recovered dichloromethane was similar to that in Example 1.

EXAMPLE 4

In Balance Synthesis of 1,4-PEKK

Figure 3:
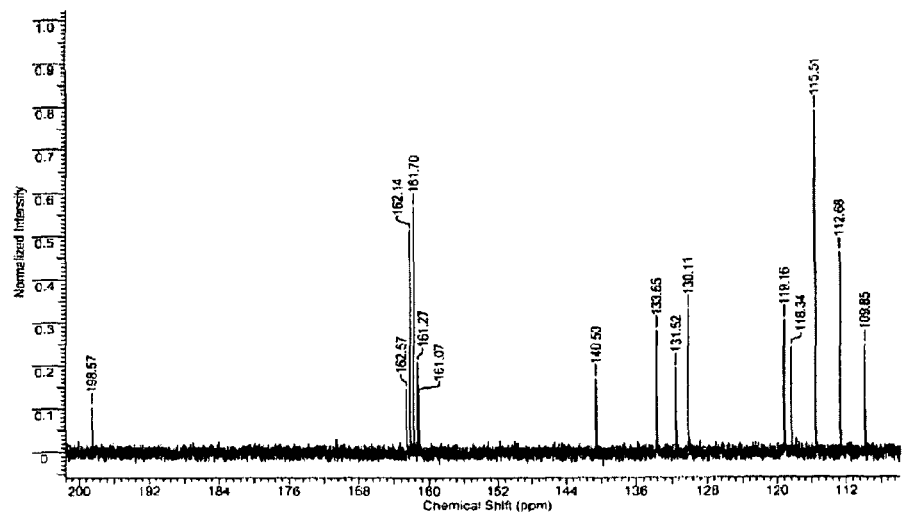
FIG. 3 illustrate $^{13}C$ NMR spectrum of 1,4-PEKK (100:0) in $CDC1_3/CF_3COOH$.

The technique used was identical to that described in Example 1. The reagents used were:
1,4-bis(4-phenoxybenzoyl)benzene: 41.5608 g (0.08833 mol)
Terephthaloyl chloride: 17.9328 g (0.08833 mol)
Benzoic acid: 31.75 g (0.26 mol)
Aluminium trichloride: 98 g (0.7344 mol)
Benzoyl chloride: 0.6747 g (4.8×10$^{−3}$ mol)
Dichloromethane: 450 ml The IV of the resultant polymer was 3.4 dL/g. The structure was confirmed by $^{13}$C NMR spectroscopy as shown in FIG. 3. This shows the $^{13}$C NMR spectrum of 1,4-PEKK (100:0) in CDCl$_3$/CF$_3$COOH. The 100:0 PEKK polymer structure comprises seven carbon atoms in unique chemical environments (see below) and hence seven resonances are expected. The following seven lines in the spectrum are assigned to the polymer; all in ppm −119.16, 130.11, 131.52, 133.65, 140.50, 161.27, 198.57. The other resonances are due to trifluoroacetic acid.

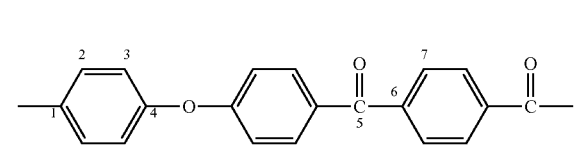

EXAMPLE 5

Synthesis of 70:30 PEKK 4% out of Balance

The technique used was identical to that described in Example 2. The reagents used were:
1,4-bis(4-phenoxybenzoyl)benzene: 52.6512 g (0.1119 mol)
Mixture of iso and terephthaloyl chlorides: 21.8092 g (0.1074 mol).
  Isophthaloyl chloride: 13.3567 g (0.0416 mol)
  Terephthaloyl chloride: 8.4525 g (0.0416 mol)
Benzoic acid: 52.475 g (0.4297 mol)
Benzoyl chloride: 1.2651 g (0.009 mol)
Aluminium trichloride 140.6 g (1.05 mol)
The IV of the resulting polymer was 0.96 dL/g

EXAMPLE 6

Decreasing the Tere:Iso Ratio in PEKK

Example 5 was repeated with 60:40 and 50:50 terephthaloyl:isophthaloyl ratios. The products were fine powders.

EXAMPLE 7

Example 5 was also repeated by replacing some of the 1,4-bis(4-phenoxybenzoyl)benzene with 1,3-bis(4-phenoxybenzoyl)benzene. In this way powdered PEKK can be synthesised in which the isophthaloyl content is in excess e.g. 40:60, 30:70 etc.

EXAMPLE 8

Controlling Particle Size

Sample 25, 70:30 PEKK 5% out of balance, was prepared using the following reagents and method.
1,4-bis(4-phenoxybenzoyl)benzene: 33.8184 g (0.071875 mol)
Mixture of iso and terephthaloyl chlorides: 15.36 g (0.07566 mol)
  Isophthaloyl chloride: 8.9329 g (0.044 mol)
  Terephthaloyl chloride: 6.4271 g (0.03166 mol)
Benzoic acid: 46.41 g (0.38 mol)
4-Phenoxybenzophenone (end-capper) 2.0766 g (0.00757 mol)
Aluminium trichloride 108.0 g (0.81 mol)
Dichloromethane 500 ml To a 700 ml reaction flask equipped with a mechanical stirrer, having been purged with dry nitrogen, was added 300 ml of dichloromethane. Having cooled the dichloromethane to −20° C. the aluminium trichloride was added. Still at −20° C., and whilst stirring, the benzoic acid was added keeping the temperature below −15° C. On cooling back to −20° C. the 1,4-bis(4-phenoxybenzoyl)benzene was added and residues washed into the flask using 50 ml of dichloromethane. Also at −20° C., the combined acid chlorides (i.e. the mixture of iso and terephthaloyl chlorides) were added and residues washed into the flask with 50 ml of dichloromethane. Finally, the end-capper was added and washed into the reaction flask with 25 ml of dichloromethane.

On completion of the additions the stirring speed was increased to 300 rpm and the reaction mixture allowed to warm to +25° C. During this period, the colour of the reaction mass changed from yellow to pale orange. As the mass showed signs of phase separating, the speed of the stirrer was raised to 400 rpm and this speed was maintained for the duration of the synthesis. During the polymerisation, hydrogen chloride was evolved which was trapped and disposed of safely.

After stirring at room temperature for 5 hours the reaction mass was poured into 5 litres of iced water (care must be taken to avoid the temperature of the decomplexing mixture rising above room temperature). The aqueous mass was then stirred at room temperature for 4 hours or until all of the orange colouration had disappeared leaving a snow white mass.

Having transferred the white mass to a suitable vessel, the vessel was heated and the dichloromethane distilled off. The yield of the recovered dichloromethane was 94% by weight. Having removed all of the dichloromethane, the mass was brought to reflux and refluxed for 1 hour whereupon the suspension was filtered whilst hot. While the filtrate was left to cool the white polymer solid was added to a further 3 litres of deionised water and brought to reflux. This was repeated a further two times and in each case the filtrate was added to the initial filtrate and allowed to cool. The polymer powder was then dried overnight at 150° C. under a partial vacuum. On cooling, benzoic acid crystallised from the combined filtrates. The yield of benzoic acid was enhanced by chilling the filtrates to 5° C. The yield of the recovered benzoic acid was 75% by weight.

The Inherent Viscosity (IV) of the polymer was determined by dissolving approximately 25 mg of the polymer in 25 ml of concentrated sulphuric acid at 25° C. The IV of this sample was 0.88 dL/g. The structure of the polymer was confirmed by $^{13}$C NMR.

The above method was carried out using the following reagents in order to produce Sample 24 which was 80:20 PEKK 3% out of balance
1,4-bis(4-phenoxybenzoyl)benzene: 100 g (0.2125 mol)
Mixture of iso and terephthaloyl chlorides: 41.8535 g (0.2062 mol)
  Isophthaloyl chloride: 17.0009 g (0.0837 mol)
  Terephthaloyl chloride: 24.8526 g (0.1224 mol)
Benzoic acid: 100.75 g (0.825 mol)
Benzoyl chloride (end capper) 1.7712 g (0.0126 mol)
$AlCl_3$ 268 g (2.01 mol)
Dichloromethane 1000 ml The Inherent Viscosity (IV) of the polymer was determined by dissolving approximately 25 mg of the polymer in 25 ml of concentrated sulphuric acid at 25° C. The IV of this sample was 1.01 dL/g. The structure of the polymer was confirmed by $^{13}$C NMR.

Sample 25 was produced using 2 moles of benzoic acid per mole of acid halide groups in the phthaloyl chlorides, whereas Sample 24 was produced using 1.5 moles of benzoic acid per mole of acid halide groups in the phthaloyl chlorides. The effect of the amount of controlling agent was investigated by analysing the particle size distribution using a Malvern Instruments Mastersizer 2000. The size distribution was determined by dispersing approximately 1 g of PEKK powder in 500 ml of a liquid carrier, this may be water, propan-2-ol or some other liquid carrier, and using this dispersion for use in the Mastersizer. The samples were all ultrasonically treated prior to the analysis to ensure agglomerates are broken up. For Sample 25, which was prepared using the higher proportion of controlling agent, 79% (by volume) of the particles were below 100 μm in diameter and 61% were below 70 μm. In comparison, for Sample 24 only 54% were below 100 μm in diameter and only 28% were below 70 μm. The volume weighted mean particle diameter for Sample 25 was 87 μm and for Sample 24 it was 109 μm.

EXAMPLE 9

Spherical Particles

FIG. 4 shows a photograph taken using a Nikon Eclipse E400 optical microscope of a sample of the dried polymer powder of Sample 24 on a microscope slide as it came out of the reactor. The particles received no post-polymerisation treatment other than the standard work-up process.

What is claimed is:

1. A method of preparing a poly (ether ketone ketone) consisting essentially of the repeat unit:

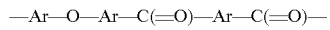

wherein each Ar is independently an aromatic moiety,
said method comprising polymerising a monomer system in a reaction medium comprising:
(a) a Lewis acid; and
(b) a controlling agent comprising an aromatic carboxylic acid, an aromatic sulphonic acid, or a derivative thereof.

2. A method for producing a poly (ether ketone ketone) consisting essentially of the repeat unit:

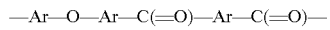

wherein each Ar is independently an aromatic moiety, having a selected particle size distribution, said method comprising:
(i) polymerising a monomer system in a reaction medium comprising:
(a) a Lewis acid; and
(b) a controlling agent comprising an aromatic carboxylic acid, an aromatic sulphonic acid, or a derivative thereof
and
(ii) adjusting a ratio of controlling agent to monomers in the monomer system whereby to control particle size distribution.

3. The method as claimed in claim 2 wherein the particle size is selected by adjusting a ratio of moles of controlling agent to moles of acid halide groups present in the monomer system.

4. The method as claimed in claim 1 wherein the ratio of moles of controlling agent to moles of acid halide groups present in the monomer system is from 0.1 to 10.

5. The method as claimed in claim 1 wherein the controlling agent comprises:

(i) $Ar'(COOX)_y$;
(ii) $Ar'(SO_3X)_y$;
(iii) $(Ar'COO^-)_z M^{z+}$; or
(iv) $(Ar'SO_3^-)_z M^{z+}$ wherein Ar' is an aromatic group compatible with the remaining components of the reaction medium;
each X independently is a hydrogen atom or an organic group (R);
each y independently is 1, 2 or 3;
each M independently is a metal ion; and
each z independently is an integer equal to the charge on the metal ion ($M^{z+}$).

6. The method as claimed in claim 1 wherein each Ar is independently selected from substituted and unsubstituted phenylene and substituted and unsubstituted polynuclear aromatic moieties.

7. The method as claimed in claim 1 wherein said Lewis acid is aluminium chloride.

8. The method as claimed in claim 1 wherein said controlling agent is benzoic acid.

9. The method as claimed in claim 1 wherein said monomer system comprises bis 1,4(4-phenoxybenzoyl)benzene and a phthaloyl halide in a 1:1 ratio by weight.

10. The method as claimed in claim 9 wherein said phthaloyl halide is a mixture of terephthaloyl halide and isophthaloyl halide.

11. The method as claimed in claim 9 wherein said phthaloyl halide is phthaloyl chloride.

12. The method as claimed in claim 10 wherein a ratio of terephthaloyl halide to isophthaloyl halide is 60:40 by weight.

13. The method as claimed in claim 1, wherein the poly (ether ketone ketone) is in particulate form.

14. The method of claim 13, wherein said particulate form comprises substantially spherical particles.

15. The method as claimed in claim 13, wherein the particulate form comprises particles, which are 0.1 to 3000 μm in diameter.

16. The method as claimed in claim 13, wherein at least 25% of the particles in the particulate form are less than 100 μm in diameter.

17. The method as claimed in claim 1, further comprising forming said poly (ether ketone ketone) into an article selected from the group consisting of a biomedical implant, a film, a fibre, or an aerospace component.

* * * * *